(12) United States Patent
Wood et al.

(10) Patent No.: US 9,750,931 B2
(45) Date of Patent: Sep. 5, 2017

(54) INTERVENTIONAL MEDICAL SYSTEMS, ASSEMBLIES AND METHODS

(71) Applicant: Medtronic, Inc., Minneapolis, MN (US)

(72) Inventors: Rónán Wood, Co. na Gaillimhe (IE); Sean Ward, Dublin (IE); James M Keaveney, Galway (IE)

(73) Assignee: Medtronic, Inc., Minneapolis, MN (US)

(*) Notice: Subject to any disclaimer, the term of this patent is extended or adjusted under 35 U.S.C. 154(b) by 195 days.

(21) Appl. No.: 14/620,904

(22) Filed: Feb. 12, 2015

(65) Prior Publication Data

US 2016/0235971 A1 Aug. 18, 2016

(51) Int. Cl.
*A61N 1/00* (2006.01)
*A61N 1/05* (2006.01)
(Continued)

(52) U.S. Cl.
CPC ........ *A61N 1/0573* (2013.01); *A61B 17/3468* (2013.01); *A61N 1/362* (2013.01);
(Continued)

(58) Field of Classification Search
CPC ...... A61N 1/0573; A61N 1/362; A61N 1/372; A61N 1/37205; A61N 1/3756; A61N 2001/058; A61B 17/3468
See application file for complete search history.

(56) References Cited

U.S. PATENT DOCUMENTS

| 5,037,427 A | 8/1991 | Harada et al. |
| 8,348,952 B2 | 1/2013 | Sanders et al. |

(Continued)

FOREIGN PATENT DOCUMENTS

| WO | 2009/099464 A1 | 8/2009 |
| WO | 2013/062793 A1 | 5/2013 |
| WO | 2013/074780 A1 | 5/2013 |

OTHER PUBLICATIONS (PCT/US2016/016785) PCT Notification of Transmittal of the International Search Report and the Written Opinion of the International Searching Authority, mailed Jul. 18, 2016, 11 pages.
(Continued)

*Primary Examiner* — Mallika D Fairchild

(57) ABSTRACT

A system for delivering an implantable medical device includes a loading assembly and a catheter. The loading assembly includes a deployment member and a sidewall defining a chamber into which the device may be pulled through a distal opening thereof, so that the sidewall holds fingers of the device's fixation member in an extended condition while a temperature in the chamber is lowered. When the chamber is connected to the catheter, advancing the deployment member pushes the device, with fixation fingers in the extended condition, into a delivery lumen of the catheter. With the catheter positioned within a patient, the device can be pushed into a distal portion of the catheter while a relatively cold fluid is infused through the delivery lumen. While holding the deployment member in place, retracting the catheter exposes the device fixation fingers out from the lumen, for engagement with tissue at the implant site.

10 Claims, 9 Drawing Sheets

(51) Int. Cl.
    *A61B 17/34*     (2006.01)
    *A61N 1/372*     (2006.01)
    *A61N 1/362*     (2006.01)
    *A61N 1/375*     (2006.01)

(52) U.S. Cl.
    CPC ............ *A61N 1/372* (2013.01); *A61N 1/3756* (2013.01); *A61N 1/37205* (2013.01); *A61N 2001/058* (2013.01)

(56) References Cited

U.S. PATENT DOCUMENTS

| | | |
|---|---|---|
| 8,721,587 B2 | 5/2014 | Berthiaume et al. |
| 8,758,365 B2 | 6/2014 | Bonner et al. |
| 2002/0177899 A1 | 11/2002 | Eum et al. |
| 2006/0085041 A1 | 4/2006 | Hastings et al. |
| 2012/0172892 A1 | 7/2012 | Grubac et al. |
| 2013/0079798 A1 | 3/2013 | Tran et al. |
| 2013/0103047 A1* | 4/2013 | Steingisser ......... A61N 1/3756 606/129 |
| 2013/0131693 A1 | 5/2013 | Berthiaume et al. |
| 2013/0253346 A1 | 9/2013 | Griswold et al. |
| 2016/0067447 A1* | 3/2016 | Paspa ................ A61N 1/05 606/129 |

OTHER PUBLICATIONS

U.S. Appl. No. 14/518,211, filed Oct. 20, 2014.
U.S. Appl. No. 14/518,261, filed Oct. 20, 2014.
U.S. Appl. No. 14/242,123, filed Apr. 1, 2014.

\* cited by examiner

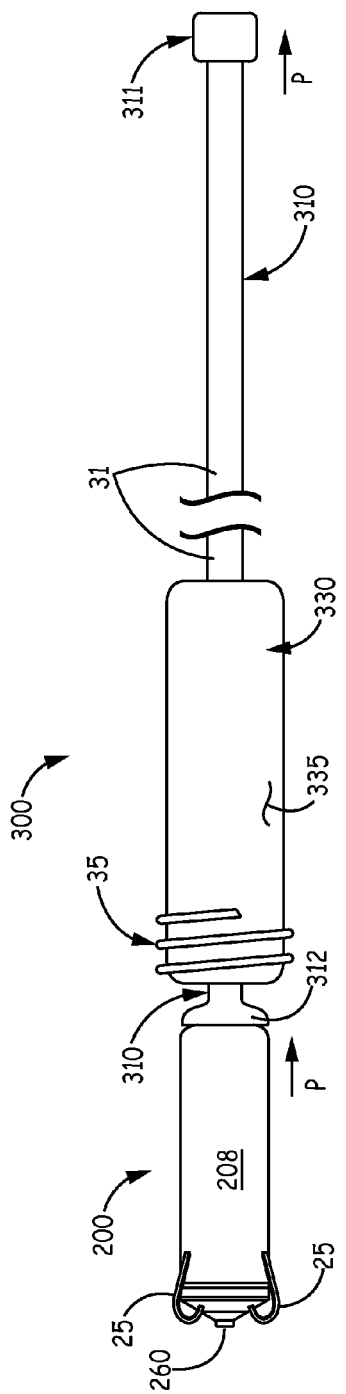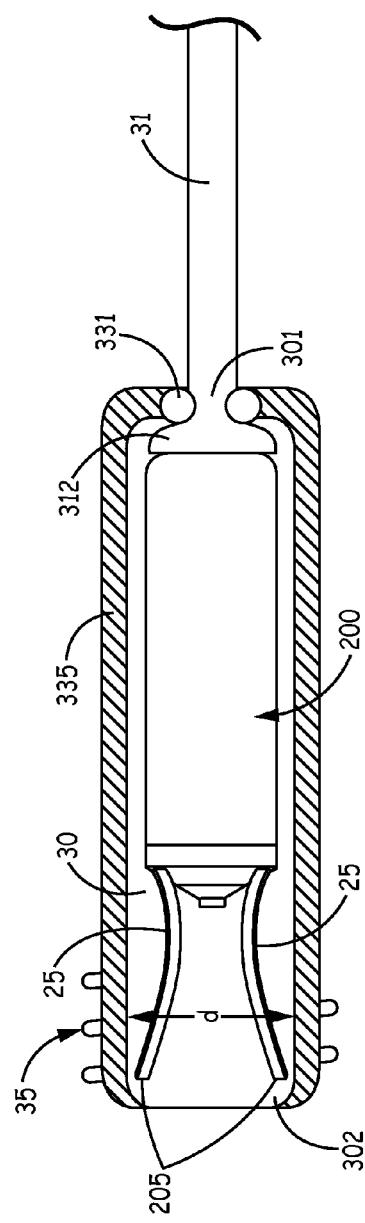

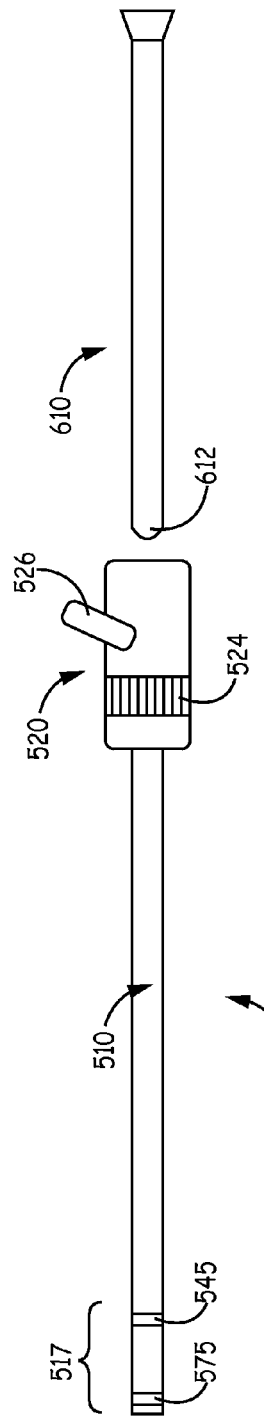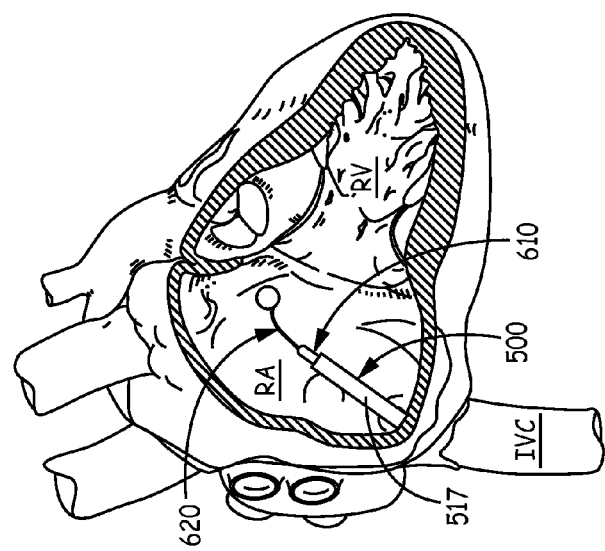

INTERVENTIONAL MEDICAL SYSTEMS, ASSEMBLIES AND METHODS

FIELD OF THE DISCLOSURE

The present disclosure pertains to interventional medical systems, and more particularly to systems, assemblies and methods useful for delivering an implantable medical device to an implant site.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV. An implanting physician may employ a standard guiding catheter (not shown) to deliver a relatively compact medical device to any one of the three exemplary sites, for example, according to methods known in the art of interventional cardiology, by maneuvering the catheter, with the device loaded therein, up through the inferior vena cava IVC and into the right atrium RA. However, there is still a need for new interventional medical systems, assemblies and methods that increase the ease and efficiency of delivering such an implantable medical device to an implant site.

SUMMARY

An interventional medical system for delivering an implantable medical device to an implant site, according to some embodiments, includes a loading assembly and a delivery catheter, configured for connection with one another. In some embodiments, the loading assembly includes a deployment member and a capsule, wherein the capsule has a sidewall defining a chamber of a size to contain the medical device while holding fingers of a fixation member of the device in an extended condition, and the deployment member includes an elongate shaft and an enlarged distal-most end, which is coupled thereto. The enlarged distal-most end, according to some embodiments, is configured to engage around a proximal end of a housing of the medical device, and the shaft extends through a proximal opening of the capsule chamber, which is formed by a seal member that is configured for sliding and sealing engagement around the shaft, so that the deployment member can be moved relative to the capsule, to pull the device into the chamber and to push the device out from the chamber through a distal opening thereof.

According to some methods, after an operator pulls the implantable medical device into the capsule chamber of the loading assembly, through the distal opening thereof, so that the sidewall of the capsule holds the device fixation fingers in the extended condition while a temperature in the chamber is lowered, the operator connects the chamber of the loading assembly to a handle of the delivery catheter and then advances the loading assembly deployment member to push the device, with the fixation fingers in the extended condition, out though the distal opening of the chamber and into a device delivery lumen of the delivery catheter, thereby loading the device into the delivery catheter. The temperature in the chamber of the loading assembly may be lowered either before or after connecting the chamber to the delivery catheter handle.

After positioning the delivery catheter within a venous system of a patient, the operator may continue to advance the deployment member of the loading assembly to push the device into a distal portion of the catheter while a relatively cold fluid, which keeps the device fixation member fingers in the extended condition, is infused through the device delivery lumen, for example via an infusion port of the handle. Once the operator has navigated the distal portion of the catheter to an implant site, so that a device exit port of the device delivery lumen is located in close proximity thereto, the operator can retract the delivery catheter while holding the deployment member in place, the distal-most end of which still engages the proximal end of the device housing, to expose the device fixation fingers out through the exit port of the delivery lumen, for engagement with tissue at the implant site.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIGS. 3A-B are plan views of a loading assembly engaged with the exemplary medical device, according to some embodiments and methods;

FIGS. 6A-D are various views and schematics outlining methods for employing the system that includes the loading assembly of FIGS. 3A-B, and the catheter of FIGS. 5A-B.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
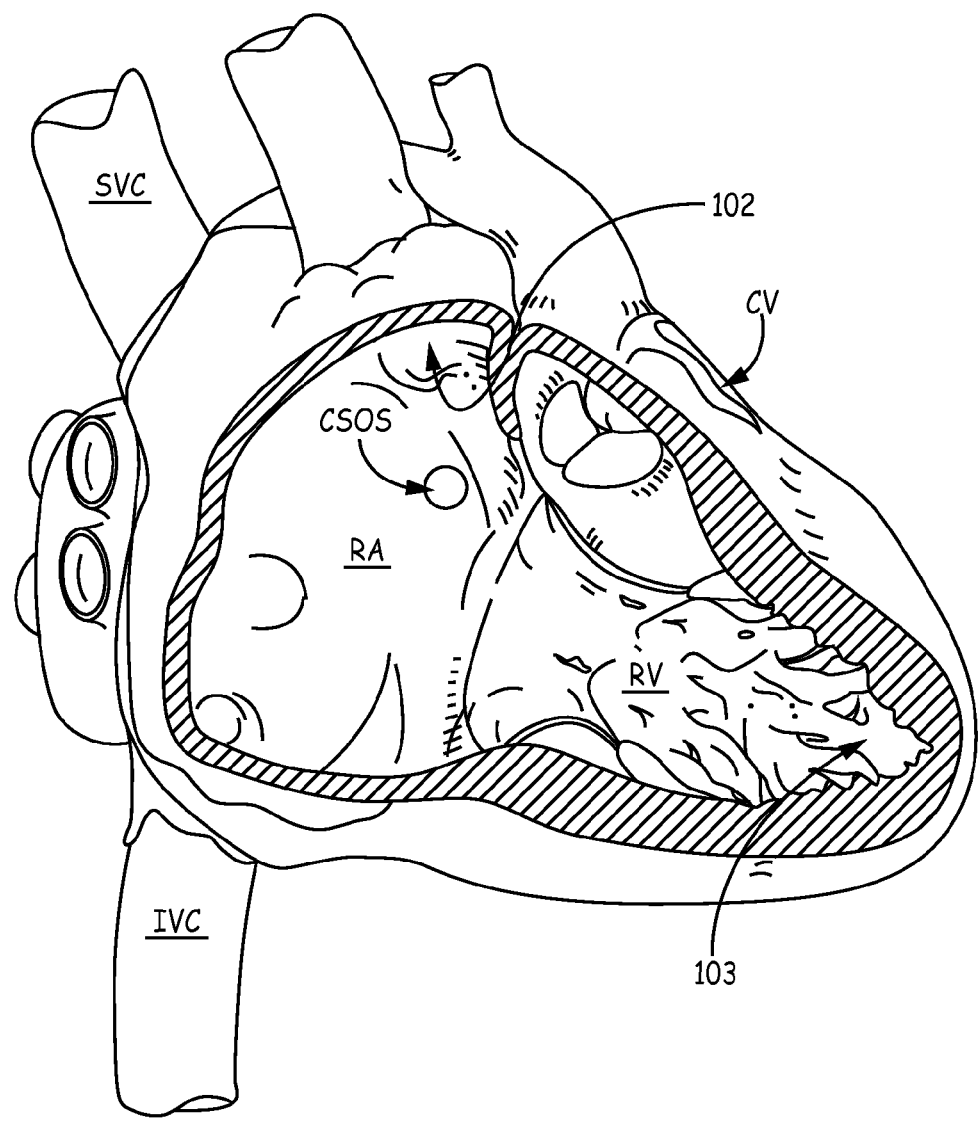
FIG. 1 is a schematic diagram showing potential implant sites for a relatively compact implantable medical device.
Figure 2:
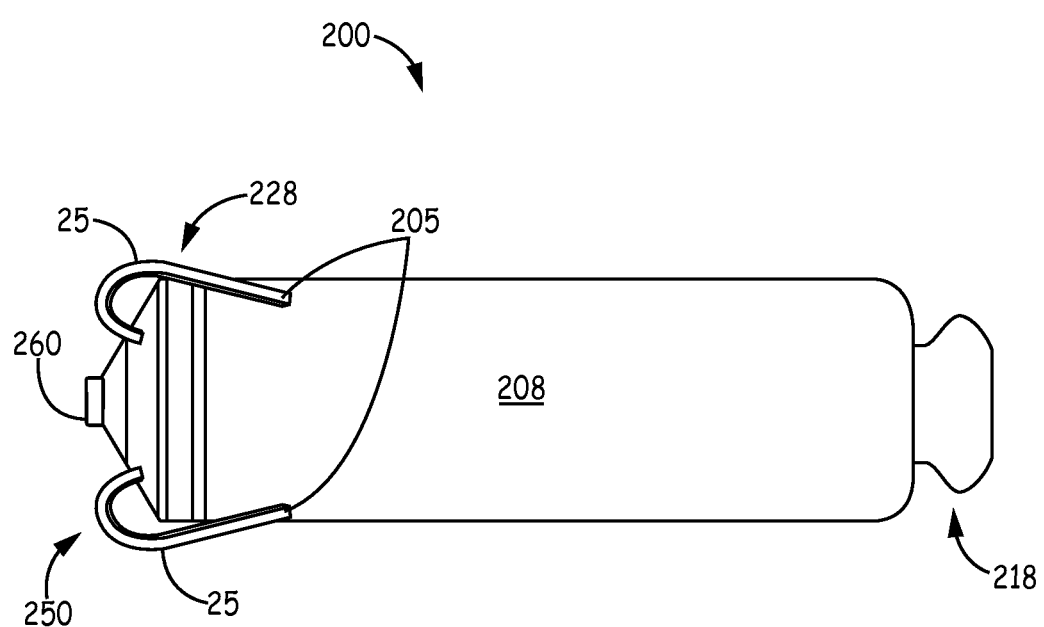
FIG. 2 is a plan view of an exemplary relatively compact implantable medical device.

FIG. 2 is a plan view of an exemplary relatively compact implantable medical device 200 suitable for implant in any of the locations described above in conjunction with FIG. 1. FIG. 2 illustrates device 200 including a hermetically sealed housing 208, for example, formed from a biocompatible and biostable metal such as titanium, and an electrode 260 and a fixation member 250, both mounted in proximity to a distal end 228 of housing 208. Device 200 further includes an electronic controller (not shown), for example, a pulse generator and an associated power supply, contained in housing 208, wherein electrode 260 is electrically coupled to the controller via a hermetically sealed feedthrough assembly (not shown) such as is known in the art. Housing 208 may be overlaid with an insulative layer, for example, medical grade polyurethane, parylene, or silicone, and, although not shown, device 200 may include another electrode, for example, formed by removing a portion of the insulative layer to expose the metallic surface of housing 208. The other electrode may function in conjunction with electrode 260 for bipolar pacing and sensing, when fixation member 250 secures electrode 260 in intimate tissue contact at a target implant site.

With further reference to FIG. 2, device fixation member 250 includes a plurality of fingers 25 spaced apart from one another around a perimeter of device housing distal end 225. Although only two fingers 25 of fixation member 250 are shown in FIG. 2, fixation member 250 may include as many as eight fingers 25. According to an exemplary embodiment, each fixation finger 25 has a thickness of approximately 0.005 inch, and fixation fingers 25 are integrally formed with one another, having been cut from Nitinol tubing, according to methods known in the art. After cutting the Nitinol tubing, fingers 25 may be shaped by bending and holding fingers 25 in the illustrated curvature while heat treating, according to methods known to those skilled in the art. Fixation member 250 may be mounted to distal end 228 of device housing 208, for example, in a manner similar to that described for a fixation component 102 in co-pending and commonly assigned United States Patent Application 2012/0172690, which description is hereby incorporated by reference. The super-elastic nature of Nitinol allows fingers 25 to elastically deform between a relaxed condition, which is shown, and an extended condition, in which a free end 205 of each finger extends distally away from distal end 228 of device housing 208. The extended condition of fingers 25, which is described in greater detail below, allows for initial engagement of fingers 25 with tissue, when device 200 is deployed at an implant site, for example, in any of the locations described above in conjunction with FIG. 1.

FIG. 3A is a plan view of a loading assembly 300 engaged with device 200, according to some embodiments and methods of the present invention. FIG. 3A illustrates loading assembly 300 including a deployment member 310 and a capsule 330, wherein an enlarged distal-most end 312 of deployment member 310, which is coupled to a shaft 31 of deployment member 310, is engaged around a proximal end 218 of device housing 208 to pull device 200, per arrow P, into a chamber 30 of capsule 330, which can be seen in the partial cross-section view of the plan view of FIG. 3B. FIG. 3B illustrates chamber 30 of capsule 330 being defined by a sidewall 335 that holds fingers 25 of fixation member 250 in the above-described extended condition, and being sized to contain therein device 200 engaged with distal-most end 312 of deployment member 310. Capsule sidewall 335 may be formed, for example, by injection molding, from any suitable hard plastic, such as a polyether block amide, for example, PEBAX® 7233. FIGS. 3A-B further illustrate capsule 330 of loading assembly 300 including a connector 35, which is formed around a distal opening 302 of chamber 30, and a seal member 331 that forms a proximal opening 301 of chamber 30. According to the illustrated embodiment, seal member 331, for example, an O-ring type seal formed from a medical grade silicone rubber, is configured for sealing and sliding engagement around shaft 31 of deployment member 310, so that an operator can move shaft 31 back and forth through proximal opening 301. It should be noted that enlarged distal-most end 312 is preferably sized to prevent passage thereof through proximal opening 301 of chamber 30. According to an exemplary embodiment, shaft 31 is formed from any relatively flexible and biocompatible material, such as stainless steel braid-reinforced PEBAX® 3533, and distal-most end 312 of the same material or a somewhat stiffer material, for example PEBAX® 7233.

Figure 3C:
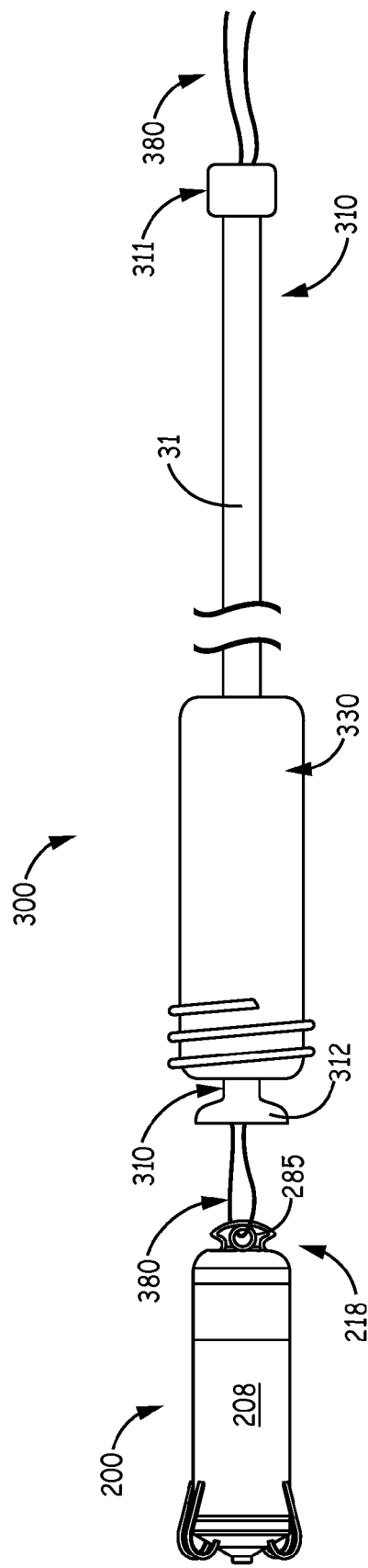
FIG. 3C is a plan view of the loading assembly including a tether engaged with the medical device, according to some alternate embodiments and methods.

With reference back to FIG. 2, proximal end 218 of device housing 208 is shown having a configuration that may facilitate a snap-fit of distal-most end 312 of deployment member 310 thereabout so that the operator can use deployment member 310 to apply a pull force to device 200. Alternately, with reference to FIG. 3C, proximal end 218 may be formed to include a tether catch 285 to which the operator may attach an optional tether 380 of deployment member 310 to engage device 200 with distal-most end 312 of deployment member 310. FIG. 3C shows tether 380 being looped within optional lumens (not shown) of deployment member 310 such that opposing ends thereof protrude from a proximal end 311 of shaft 31 and are accessible for the operator to grasp and pull on tether 380 for engaging device 200 with distal-most end 312.

With further reference to FIG. 3A, according to some preferred methods, the operator, after engaging distal-most end 312 around device proximal end 218, can grasp shaft 31, for example, in proximity to proximal end 311, to pull, per arrow P, the engaged device 200 through distal opening 302 of chamber 30 so that sidewall 335 moves device fixation fingers 25 from the relaxed condition to the extended condition and then holds fingers 25 in the extended condition while containing device 200 in chamber 30. According to an exemplary embodiment, a diameter d (FIG. 3B) of chamber 30 is approximately 0.272 inch. If deployment member 310 includes tether 380, the operator may hold the tether taut to keep device housing 208 engaged with distal-most end 312 of deployment member 310, while pulling device 200 into chamber 30 of capsule 330.

Figure 4:
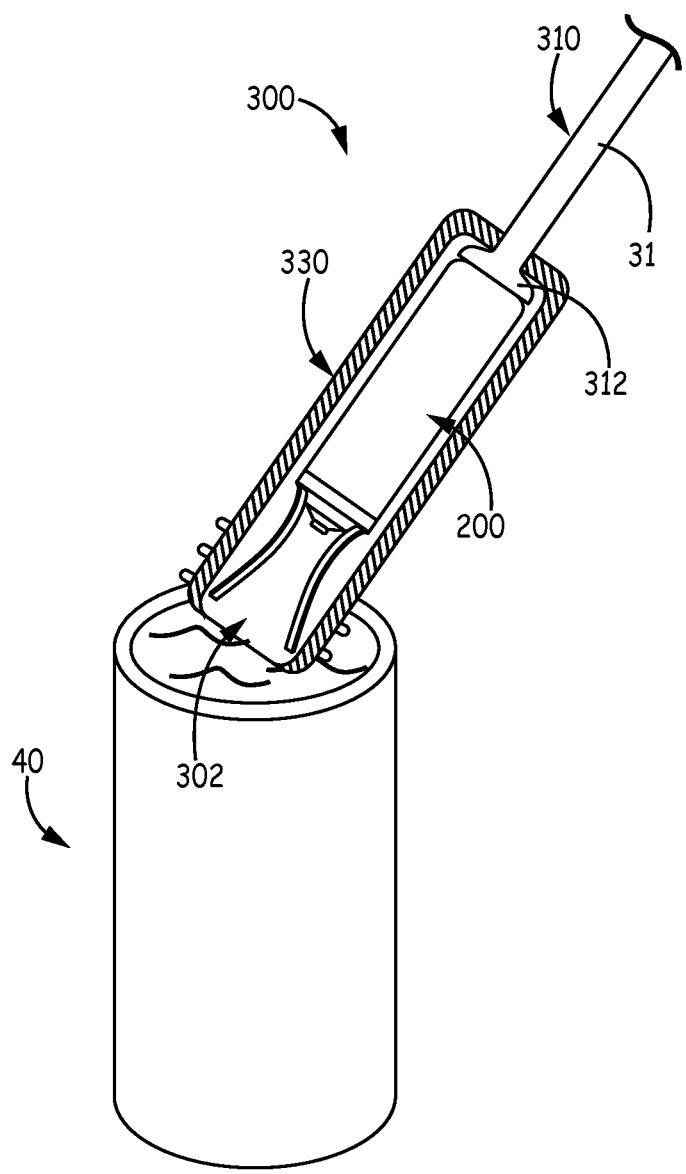
FIG. 4 is a schematic depicting an exemplary method for lowering a temperature within a chamber of a loading assembly, like the loading assembly of FIGS. 3A-B.

Due to the shape-memory nature of Nitinol, from which fingers 25 are preferably formed, fingers 25, once moved into the extended condition by capsule sidewall 335, may remain in the extended condition without the support of sidewall 335, if a temperature of fingers 25 is lowered to approximately 5° C. to 15° C., or lower. FIG. 4 is a schematic depicting an exemplary method for lowering a temperature within chamber 30 of loading assembly 300 to cool fingers 25, so that fingers 25 may remain in the extended condition when the operator moves device 200 out from loading assembly 300 and into a slightly larger diameter lumen of a catheter, for example, a device delivery lumen 50 of a delivery catheter 500 shown in FIGS. 5A-B. FIG. 4 illustrates capsule 330, with device 200 contained therein, being immersed into a container of fluid 40, for example, a chilled saline solution, which has a sufficiently low temperature to lower the temperature of fingers to at or below approximately 5° C. to 15° C. According to some methods, after the operator immerses capsule 330 into fluid 40, so that the fluid fills chamber 30 and cools fingers 25, the operator connects capsule 330 to a handle 520 of delivery catheter 500, by mating connector 35 of capsule to a connector 55 of handle 520. Alternative and subsequent method steps for loading device into delivery catheter will be described below, in conjunction with FIG. 6C.

Figure 5A:
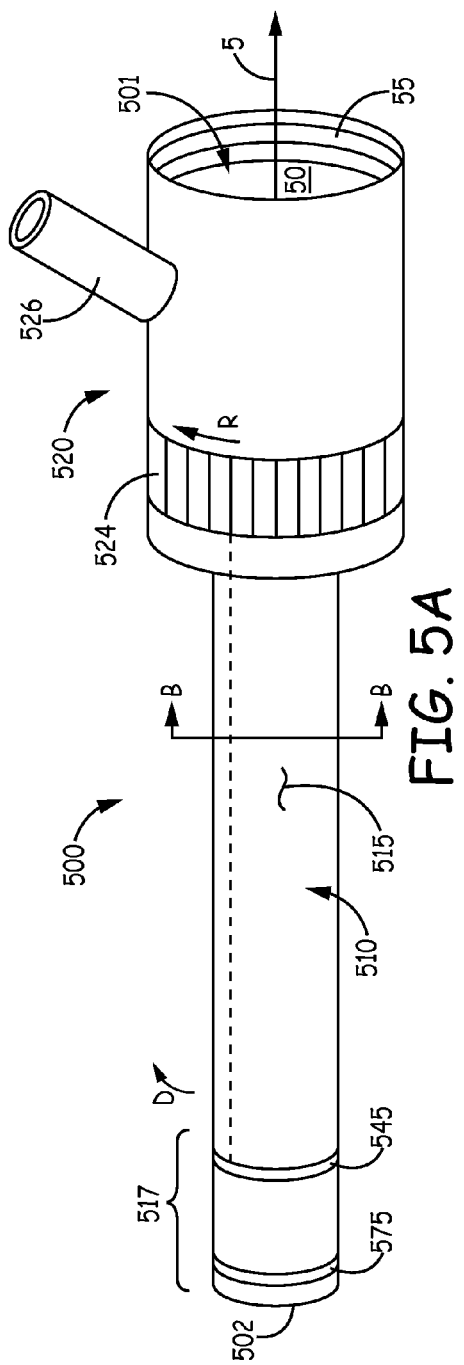
FIG. 5A is a perspective view of a delivery catheter for use in a system with the loading assembly of FIGS. 3A-B, according to some methods and embodiments.
Figure 5B:
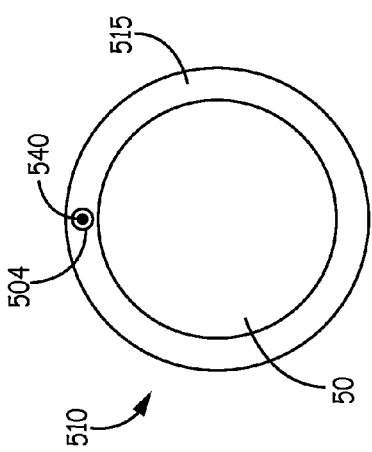
FIG. 5B is an axial cross-section through section line B-B of FIG. 5A, according to some embodiments.

FIGS. 5A-B illustrate delivery catheter 500 including an elongate tube 510, which, along with handle 520, defines device delivery lumen 50 that extends from a device entry port 501, around which connector 55 is formed, to a device exit port 502 that terminates a distal portion 517 of tube 510. FIGS. 5A-B further illustrate a deflection wire assembly of delivery catheter 500 including a deflection wire 540 (shown with a dashed line in FIG. 5A) extending along a length of tube 510 and being contained within a sidewall 515 thereof (e.g., within a lumen 504 thereof), a control member 524 mounted in handle 520 and being coupled to a proximal end of wire 540, and a deflection band 545 mounted in sidewall 515 of tube 510 and being coupled to a distal end of wire 540. In FIG. 5A, a radiopaque marker band 575 is shown mounted around sidewall 515 of elongate tube 510 in proximity to device exit port 502, and deflection band 545 is shown spaced proximally therefrom. According to some embodiments, control member 524 is formed by a torque wheel, which is configured to rotate around a longitudinal axis 5 of handle 520, so that rotation of member 524, per arrow R, moves wire 540 within lumen 504 of sidewall 515 to deflect distal portion 517 of catheter tube 510, per arrow D.

FIG. 6A is a plan view of delivery catheter 500 together with a dilator 610 that is positioned in proximity to catheter handle 520. According to some methods, the operator may introduce catheter 500 into a venous system of a patient without the need of an introducer sheath, by inserting dilator 610 into device delivery lumen 50 of catheter 500, thereby stiffening tube 510 of delivery catheter 500 for the percutaneous introduction. An outer diameter of delivery catheter tube 510 may be as small as 22 F (0.29 inch/7.3 mm) to 23 F (0.30 inch/7.6 mm). To facilitate such an introduction, in some preferred embodiments, an outer surface of sidewall 515 of delivery catheter tube 510 has a hydrophilic coating formed thereover. According to some preferred methods, the operator introduces catheter 500, with dilator 610 inserted therein, over a guide wire 620 which the operator has pre-positioned in the venous system, for example, in the patients right atrium RA, as shown in FIG. 6B. Those skilled in the art are familiar with suitable constructions of guide wires and dilators for such a purpose, wherein a distal tip 612 of dilator 610 is tapered to provide a smooth transition from an outer diameter of guide wire 620 to an outer diameter of catheter tube 510. Once the operator has introduced catheter 500 and positioned distal portion 517 thereof in a desired location within the patient's venous system (e.g., the right atrium RA), the operator withdraws guide wire 620 and dilator 610 out from device delivery lumen 50 of catheter to make way for the loading of device 200 therein, as alluded to above.

Figure 6C:
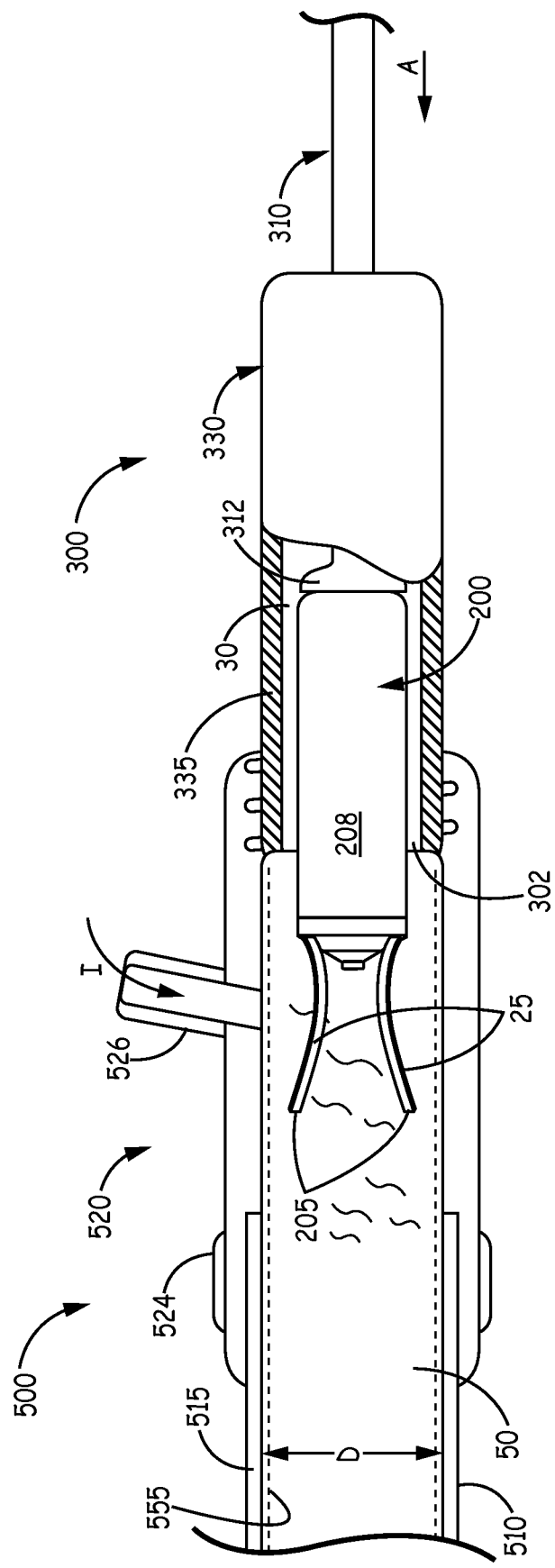

FIG. 6C is a plan view with a partial cut-away section of loading assembly 300 connected to catheter handle 520. FIG. 6C illustrates deployment member 310 of loading assembly 300 having been advanced, per arrow A, to push device 200 out through distal opening 302 of capsule 330. According to some methods, the operator has lowered a temperature within chamber 30 of capsule 330 to cool device fixation fingers 25 prior to connecting capsule 330 to handle 520, for example, by immersing capsule 330 with device 200 contained therein into container of fluid 40 as described above, in conjunction with FIG. 4. According to some alternative methods, the temperature of chamber 30 may be lowered to cool fixation fingers 25, after the operator connects capsule 330 to delivery catheter handle 520, for example, by infusing a relatively cold fluid (e.g., chilled saline solution), per arrow I, through device delivery lumen 50, for example, via an infusion port 526 of handle 520, and/or by infusing a relatively cold fluid through an optional lumen of deployment member 310. In any case, after device 200, with fixation fingers 25 in the extended condition, is pushed into device delivery lumen 50, the infusion of the relatively cold fluid through lumen 50 is continued to keep device fixation fingers 25 in the extended condition for passage through lumen 50. According to the illustrated embodiment, continued advancement, per arrow A, of loading assembly deployment member 310 allows the operator to push device 200 along delivery lumen 50 to a position within distal portion 517. According to an exemplary embodiment, sidewall 515 of delivery catheter tube 510 is formed from various grades of a polyether block amide, for example, PEBAX® having durometers ranging from approximately 55 D, along a proximal length, to approximately 35 D, along a distal length, to give tube 510 a graduated stiffness along a length thereof. A diameter D of lumen 50, along substantially the entire length of tube 510 is approximately 0.27 inch (6.8 mm), according to some preferred embodiments, and lumen 50 may have a lubricious surface 555, for example, formed by any suitable fluoropolymer coating or liner known in the art.

Figure 6D:
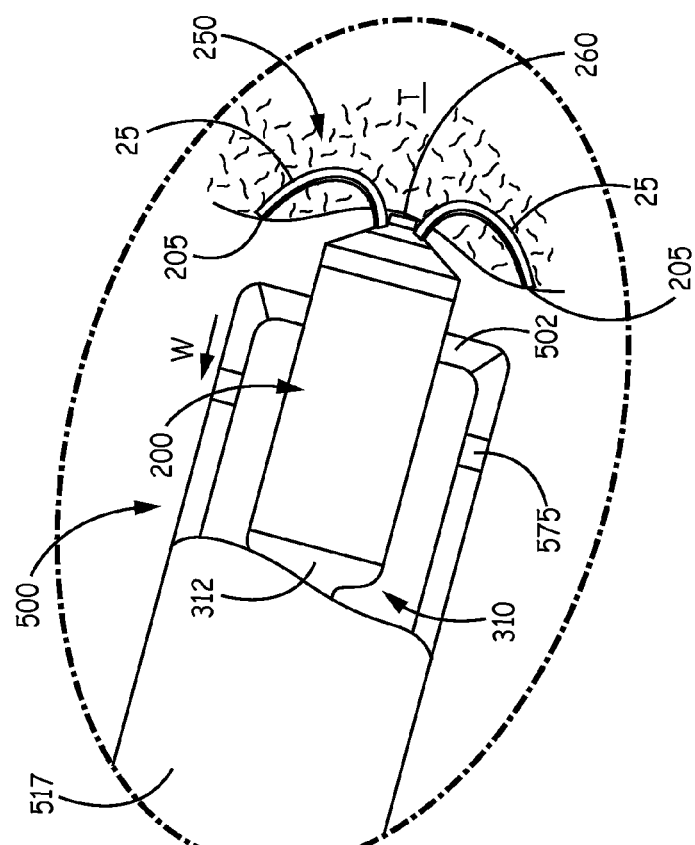
Figure 6D:
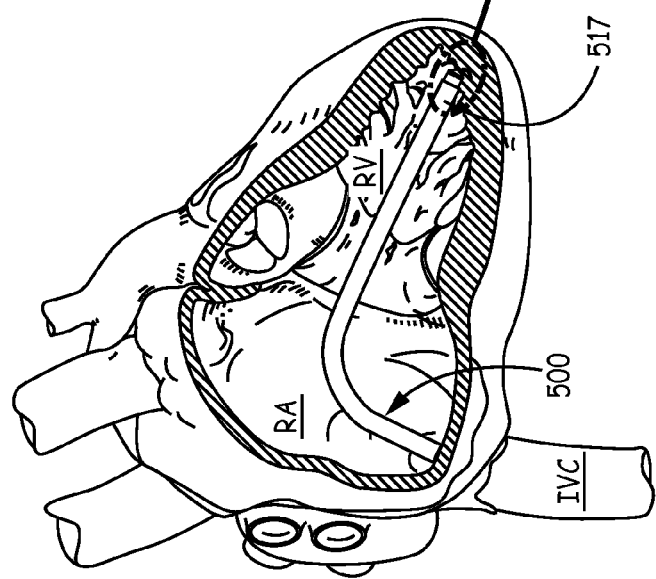

With reference to back to FIGS. 5A and 6A, according to some methods, the operator pushes the loaded device 200 in device delivery lumen 50 of catheter 500 to a location in distal portion 517 that is between deflection band 545 and marker band 575, both of which are radiopaque so that the operator may view bands 545, 575 via fluoroscopic imaging in order to position device 200 therebetween. According to an exemplary embodiment, a spacing between marker band 575 and deflection band 545 is approximately 2.5 cm. Now, with reference to FIG. 6D, once the operator has positioned device 200 between bands 545, 575, while continuing the aforementioned infusion of the relatively cold fluid through device delivery lumen 50, if the target implant site for device 200 is in the right ventricle RV, the operator navigates distal portion 517 of catheter 500 into the right ventricle RV, for example, via activation of the above-described deflection wire assembly, so that device exit port 502 is in close proximity to the implant site. FIG. 6D shows an enlarged detail of distal portion 517, wherein device fixation member fingers 25 have engaged with tissue T at the implant site. According to some methods, in order to expose fixation fingers 25 out through device exit port 502, the operator holds deployment member 310 and the engaged device 200 in place while retracting, or withdrawing delivery catheter 500, per arrow W. Free ends 205 of fingers 25 are exposed first to pierce into tissue T, and then, once fingers 25 are warmed to body temperature within tissue T, fingers 25 move toward their relaxed condition for full engagement of fixation device 250 to secure electrode 260 in intimate tissue contact as shown in FIG. 6D. It should be noted that, according to some methods, device delivery lumen 50 may be aspirated with blood, or flushed with a room temperature fluid, to warm fingers 25 just prior to withdrawing catheter 500 to expose free ends 205 thereof.

Finally, if the secured device 200 is effectively operational at the implant site, the operator can withdraw delivery catheter 500 and loading assembly 300 from the patient's venous system. But if the operator determines that device 200 needs to be removed from the implant site, the operator can withdraw loading assembly 300 out from device delivery lumen 50 of catheter 500, leaving catheter 500 in the venous system, so that device delivery lumen 50 may be employed as a passageway for a snare or other type of device capturing tool, which the operator can use to pull device 200 out from engagement with the implant site and back into delivery lumen 50.

In the foregoing detailed description, the invention has been described with reference to specific embodiments. However, it may be appreciated that various modifications and changes can be made without departing from the scope of the invention as set forth in the appended claims.

We claim:

1. An interventional medical system for delivering an implantable medical device to an implant site, the device including an electronic controller, a hermetically sealed housing containing the controller, an electrode electrically coupled to the controller and mounted in proximity to a distal end of the housing, and a fixation member mounted to the distal end of the housing, the fixation member comprising a plurality of fingers spaced apart from one another around a perimeter of the distal end of the housing, each finger being elastically deformable between a relaxed condition and an extended condition, a free end of each finger extending distally away from the distal end of the device housing, when the finger is in the extended condition, and the system comprising:

a loading assembly including a deployment member and a capsule, the deployment member including an elongate shaft and an enlarged distal-most end coupled thereto, the distal-most end being configured to engage around a proximal end of the implantable medical device housing, the capsule including a sidewall, a seal member, and a connector, the sidewall defining a chamber of a size to contain therein the implantable medical device and the distal-most end of the deployment member engaged therewith, the chamber including a proximal opening formed by the seal member and a distal opening sized for passage therethrough of the device and the distal-most end of the deployment member engaged therewith, the distal-most end being sized to prevent passage thereof through the proximal opening, the seal member being configured for sealing and sliding engagement around the shaft of the deployment member, and the connector being formed around the distal opening of the chamber; and a delivery catheter including an elongate tube and a handle coupled to a proximal end of the tube, the tube and the handle defining a device delivery lumen that extends from a device entry port formed in the handle to a device exit port that terminates a distal portion of the tube, and the handle including a connector formed around the device entry port, the connector of the handle being configured to mate with the connector of the loading assembly capsule;

wherein the size of the capsule chamber of the loading assembly is such that the sidewall holds the fingers of the device fixation member in the extended condition when the device is contained within the chamber; and when the connector of the loading assembly capsule is mated with the connector of the delivery catheter handle, the device entry port of the delivery catheter is aligned with the distal opening of the capsule chamber thereby allowing passage of the device, with the fixation fingers in the extended condition, from the chamber and into the device delivery lumen of the delivery catheter.

2. The system of claim 1, wherein the delivery catheter further includes a deflection wire assembly, the deflection wire assembly including a deflection wire, a deflection band, and a control member, the deflection wire extending along a length of the elongate tube and being contained within a sidewall thereof, the deflection band being mounted around the sidewall of the elongate tube and coupled to a distal end of the deflection wire, and the control member being mounted in the handle and coupled to a proximal end of the deflection wire.

3. The system of claim 2, wherein the deflection band is radiopaque and the delivery catheter further includes another radiopaque band mounted around the sidewall of the elongate tube in proximity to the device exit port of the device delivery lumen, the bands being spaced apart from one another along the distal portion of the tube to indicate, via fluoroscopic imaging, a location therebetween for positioning the device in the device delivery lumen of the catheter.

4. The system of claim 2, wherein the control member of the deflection wire assembly comprises a torque wheel configured to rotate around a longitudinal axis of the handle.

5. The system of claim 1, wherein the handle of the delivery catheter further includes an infusion port in fluid communication with the device delivery lumen.

6. The system of claim 1, wherein the connector of the handle of the delivery catheter comprises a female thread and the connector of the capsule of the loading assembly comprises a male thread.

7. The system of claim 1, wherein the deployment member of the loading assembly further includes a tether and a pair of lumens through which the tether extends.

8. An assembly for loading an implantable medical device into a delivery catheter, the device including an electronic controller, a hermetically sealed housing containing the controller, an electrode electrically coupled to the controller and mounted in proximity to a distal end of the housing, and a fixation member mounted to the distal end of the housing, the fixation member comprising a plurality of fingers spaced apart from one another around a perimeter of the distal end of the housing, each finger being elastically deformable between a relaxed condition and an extended condition, a free end of each finger extending distally away from the distal end of the device housing, when the finger is in the extended condition, and the delivery catheter including an elongate tube and a handle coupled to a proximal end of the tube, the tube and the handle defining a device delivery lumen, the device delivery lumen extending from a device entry port within the handle to a device exit port in proximity to a distal end of the tube, and the handle including a connector formed around the device entry port, and the assembly comprising:

a deployment member including an elongate shaft and an enlarged distal-most end coupled thereto, the distal-most end being configured to engage around a proximal end of the implantable medical device housing; and a capsule including a sidewall, a seal member, and a connector, the sidewall defining a chamber of a size to contain therein the implantable medical device and the distal-most end of the deployment member engaged therewith, the chamber including a proximal opening formed by the seal member and a distal opening sized for passage therethrough of the device and the distal-most end of the deployment member engaged therewith, the distal-most end being sized to prevent passage thereof through the proximal opening, the seal member being configured for sealing and sliding engagement around the shaft of the deployment member, and the connector being formed around the distal opening of the chamber and being configured to mate with the connector of the delivery catheter handle;

wherein the sidewall of the capsule chamber holds the fingers of the device fixation member in the extended condition when the device is contained within the chamber; and when the connector of the capsule is mated with the delivery catheter handle, the device entry port of the handle is aligned with the distal opening of the capsule chamber thereby allowing passage of the device, with the fixation fingers in the extended condition, from the chamber and into the device delivery lumen of the delivery catheter.

9. The assembly of claim 8, wherein the connector of the capsule comprises a male thread, and the connector of the handle of the delivery catheter comprises a female thread.

10. The assembly of claim 8, wherein the deployment member further includes a tether and a pair of lumens through which the tether extends.

\* \* \* \* \*